(12) United States Patent
Munshi

(10) Patent No.: US 6,856,840 B2
(45) Date of Patent: Feb. 15, 2005

(54) IONICALLY CONDUCTIVE POLYMERIC COMPOSITION

(75) Inventor: M. Zafar Amin Munshi, Missouri City, TX (US)

(73) Assignee: Intermedics, Inc., Angleton, TX (US)

( * ) Notice: Subject to any disclaimer, the term of this patent is extended or adjusted under 35 U.S.C. 154(b) by 30 days.

(21) Appl. No.: 09/921,478

(22) Filed: Aug. 3, 2001

(65) Prior Publication Data

US 2002/0019658 A1 Feb. 14, 2002

Related U.S. Application Data

(62) Division of application No. 09/042,255, filed on Mar. 13, 1998, now Pat. No. 6,295,474.

(51) Int. Cl.[7] .............................. A61N 1/05; A61N 1/04
(52) U.S. Cl. ...................... 607/121; 607/121; 607/120; 607/5; 607/7; 607/8; 252/500; 252/511; 252/518.1; 523/103; 523/122; 128/899
(58) Field of Search ................................ 252/500, 511, 252/518.1, 506, 519.32; 607/5, 7, 8, 120, 121; 604/19, 290; 128/899, 905; 427/372.2, 353, 358; 523/103, 122, 334

(56) References Cited

U.S. PATENT DOCUMENTS

| | | | |
|---|---|---|---|
| 3,357,930 A | * 12/1967 | Marks et al. ........... 252/519.31 |
| 3,865,615 A | 2/1975 | Manly ....................... 117/47 A |
| 4,281,669 A | 8/1981 | MacGregor ................. 128/784 |
| 4,326,532 A | 4/1982 | Hammar .................. 128/349 R |
| 4,355,426 A | 10/1982 | MacGregor ...................... 3/1.4 |
| 4,459,252 A | 7/1984 | MacGregor ................ 264/46.9 |
| 4,515,162 A | * 5/1985 | Yamamoto et al. ......... 600/391 |
| 4,585,652 A | 4/1986 | Miller et al. ................... 424/83 |
| 4,602,637 A | 7/1986 | Elmqvist et al. ............ 128/419 |
| 4,627,836 A | 12/1986 | MacGregor .................. 604/93 |
| 4,677,989 A | 7/1987 | Robblee ...................... 128/784 |
| 4,717,581 A | 1/1988 | Robblee ......................... 427/2 |
| 4,919,135 A | 4/1990 | Phillips, Jr. et al. ......... 128/419 |
| 5,203,348 A | 4/1993 | Dahl et al. .................. 128/784 |
| 5,227,042 A | 7/1993 | Zawodzinski et al. ....... 204/403 |
| 5,354,790 A | * 10/1994 | Keusch et al. .............. 523/300 |
| 5,409,696 A | 4/1995 | Narayanan et al. ...... 424/78.17 |

(List continued on next page.)

FOREIGN PATENT DOCUMENTS

| | | | |
|---|---|---|---|
| EP | 0051354 | 5/1982 | .......... A61M/25/00 |
| EP | 0299698 | 1/1989 | |
| EP | 0644904 | 3/1995 | |
| RU | 2086217 | * 8/1997 | ............. A61F/9/00 |
| WO | WO92/05753 | 4/1992 | |

OTHER PUBLICATIONS

Ahlswede, K.M., et al., "Microvascular Endothelial Cell Sodding of 1–mm Expanded Polytetrafluoroethylene Vascular Grafts", *Arterioscler. Thromb.*, 14, 25–31, (1994).

(List continued on next page.)

*Primary Examiner*—Yogendra N. Gupta
*Assistant Examiner*—Kallambella Vijayakumar
(74) *Attorney, Agent, or Firm*—Schwegman, Lundberg, Woessner & Kluth, P.A.

(57) ABSTRACT

An ionically conductive polymeric composition is disclosed. The composition is especially useful for coating an implantable hot can defibrillator electrode. The polymeric composition, for example, polyethylene oxide containing NaCl or a similar ionic medium, can be used to coat and fill the pores of a high surface area electrode to provide a continuous ionic network from the can to the adjacent body tissue. The conductive polymeric composition is biocompatible, chemically and mechanically stable and does not dissolve or leach out over the useful lifetime of the defibrillator. A hot can defibrillator employing the polymeric coating avoids development of high polarization at the can/tissue interface and maintains a more uniform defibrillation threshold than conventional implantable defibrillators, thus increasing the feasibility of pectoral implantation, particularly in a "dry pocket" environment.

8 Claims, 4 Drawing Sheets

U.S. PATENT DOCUMENTS

| | | | |
|---|---|---|---|
| 5,411,527 A | 5/1995 | Alt | 607/5 |
| 5,473,812 A | 12/1995 | Morris et al. | 29/825 |
| 5,480,416 A | 1/1996 | Garcia et al. | 607/36 |
| 5,488,768 A | 2/1996 | Mar | 29/860 |
| 5,512,055 A | 4/1996 | Domb et al. | 604/265 |
| 5,520,180 A * | 5/1996 | Uy et al. | 600/397 |
| 5,529,579 A | 6/1996 | Alt et al. | 607/36 |
| 5,576,072 A * | 11/1996 | Hostettler et al. | 427/532 |
| 5,601,607 A | 2/1997 | Adams | 607/5 |
| 5,654,030 A | 8/1997 | Munshi et al. | 427/2.24 |
| 5,746,616 A | 5/1998 | Mar | 439/245 |
| 5,766,527 A | 6/1998 | Schidgen et al. | 264/104 |
| 5,845,396 A | 12/1998 | Altman et al. | 29/885 |
| 5,964,794 A * | 10/1999 | Bolz et al. | 607/121 |
| 6,295,474 B1 * | 9/2001 | Munshi | 607/121 |
| 6,718,628 B2 | 4/2004 | Munshi | 29/825 |

OTHER PUBLICATIONS

Chang, Y., et al., "Assessment of an Epoxy–Filled Pericardial Patch With or Without Ionically Bound Heparin in a Canine Model", *Int. J. Artificial Organs*, 20, 332–340, (1997).

Hirigoyen, M.B., et al., "Periadventitial Delivery of Heparin in the Prevention of Microvenous Thrombosis", *J. Oral Maxillofac. Surg.*, 54, 1097–1102, (1996).

Homsy, C.S., et al., "Tissue Ingrowth Implant Fixation by a Soft Porous Coating", *Proceedings of the 34th ACEMB*, Shamrock Hilton Hotel, Houston, TX, p. 162, (Sep. 21–23, 198).

Julio, C.A., et al., "Blood Compatibility of Tubular Polymeric Materials Studied by Biological Surface Interactions", *Braz. J. Med. Biol. Res.*, 27, 2565–2568, (1994).

Keogh, J.R., et al., "Biocompatibility of Sulphonated Polyurethane Surfaces", *Biomater*, 17, 1987–1994, (1996).

Narayanan, P.V., et al., "Radiofrequency Plasma Treated Polymeric Surfaces Having Immobilized Anti–Thrombogenic Agents", U.S. Pat. No. 5409696, (1995).

Nimni, M.E., et al., "Chemically Modified Collagen: a Natural Biomaterial for Tissue Replacement", *J. Biomed. Mater. Res.*, 21, 741–771, (1987).

Tang, L., et al., "Fibrin (ogen) Mediates Acute Inflammatory Responses to Biomaterials", *J. Exp. Med.*, 178, 2147–2156, (1993).

Walton, D.G., et al., "Creation of Stable Poly(ethylene oxide) Surfaces on Poly(methyl methacrylate) Using Blends of Branched and Linear Polymers", *Macromolecules 30*, 6947–6956, (1997).

Williams, S.K., et al., "Endothelial Cell Transplantation onto Polymeric Arteriovenous Grafts Evaluated Using a Canine Model", *J. Invest. Surg.*, 7, 503–517, (1994).

Breivik, K., "Clinical Evaluation of a Thin Biopolar Pacing Lead", *PACE vol. 20*, (Mar. 1997),637–646.

Espadas–Torre, Cecilia, et al., "Thrombogenic Properties of Untreated and Poly(ethylene oxide)–Modified Polymeric Matrices Useful for Preparing Intraarterial Ion–Selective Electrodes", *Analytical Chemistry*, 67 , (Sep. 15, 1995), 3108–3114.

Olsen, Douglas A., et al., "Thrombus Formation on Polymeric Materials II. Blood Compatible Surfaces", *Minnesota Medicine*, 53, (Aug. 1970),877–884.

Dzagnidze, K., et al., "The Creation of New Polymeric Compositions with Improved Thromboresistent Properties and Their Evaluation in the Experiments in vitro", *Izv. Adad. Nauk Gruk. SSR, Ser. Khim.*, 15, (1989),306–9.

Espadas–Torre et al, "Thrombogenic Properties of Untreated and Poly(ethylene oxide)–Modified Polymeric Matrices Useful for preparing Intraarterial ion–Selective Electrodes," Anal. Chem., 1995, vol. 67, pp. 3108–3114.*

* cited by examiner

IONICALLY CONDUCTIVE POLYMERIC COMPOSITION

CROSS-REFERENCE TO RELATED APPLICATIONS

This application is a divisional of U.S. Ser. No. 09/042,255 filed Mar. 13, 1998, now U.S. Pat. No. 6,295,474 entitled Defibrillator Housing With Conductive Polymer Coating, the specification of which is hereby incorporated by reference. This application is also related to U.S. Ser. No. 09/793,000, entitled Method of Making a Stimulator Electrode With A Conductive Polymer Coating, filed on Feb. 26, 2001, also a divisional of U.S. Ser. No. 09/042,255, said application hereby incorporated by reference.

BACKGROUND OF THE INVENTION

1. Field of the Invention

The present invention generally relates to electrodes for implantable cardiac stimulators, particularly defibrillators employing a "hot can" stimulus generator housing. More particularly, the invention relates to such stimulation electrodes having a coating that protects the electrode surface from oxidation, and still more particularly to such oxidation resistant coatings that contain a conduction-enhancing medium.

2. Description of the Related Art

Abnormal rhythms or arrhythmias can arise in the heart as a consequence of an impairment of the heart's electrophysiologic properties. Tachycardia, for example, is an arrhythmia characterized by rapid beating of the affected cardiac chamber which, in some instances, may lead to fibrillation. In other instances, fibrillation may arise in a diseased heart without the advance episode of tachycardia.

During fibrillation, sections of conductive cardiac tissue of the affected chamber undergo completely uncoordinated, random contractions, quickly resulting in a loss of the blood-pumping capability of that chamber. During ventricular fibrillation (i.e., fibrillation occurring in a ventricle), cardiac output ceases instantaneously. Unless cardiac output is restored almost immediately after the onset of ventricular fibrillation, tissue begins to die for lack of oxygenated blood, and death of the patient will occur within minutes.

Because ventricular fibrillation is frequently caused by ventricular tachycardia, various methods and devices have been proposed to treat and arrest the tachycardia before the onset of fibrillation. Conventional techniques for terminating tachycardia include pacing therapy and cardioversion. In the latter technique, the heart is shocked with one or more current or voltage pulses of considerably higher energy content than is delivered in pacing pulses from a pacemaker. Unfortunately, cardioversion itself presents a considerable risk of precipitating fibrillation, as a result commonly called "refibrillation."

Defibrillation, that is, the method employed to terminate fibrillation, generally involves applying one or more high energy "countershocks" to the heart in an effort to overwhelm the chaotic contractions of individual tissue sections, thereby restoring the synchronized contractions of the atria and ventricles. Successful defibrillation requires the delivery to the heart of the afflicted person an electrical pulse containing energy at least adequate to terminate the fibrillation and to preclude refibrillation. Although high intensity defibrillation shocks are often successful in arresting fibrillation, they tend to precipitate cardiac arrhythmias, which themselves may accelerate into fibrillation, i.e., refibrillation. Additionally, high intensity shocks can cause permanent injury to the lining of the heart (myocardium).

In the conventional approach of external defibrillation, conducting paddles or electrodes are positioned on the patient's chest and electrical energy typically in the range of 100 to 400 joules is delivered to the chest area in the region of the heart. When fibrillation occurs during open heart surgery, internal paddles may be applied to opposite surfaces of the ventricular myocardium, and the energy required for defibrillation is considerably less, on the order of 20 to 40 joules.

More recently, implantable defibrillators have been developed for use in detecting and automatically treating ventricular fibrillation. In the last twenty years, a vast number of improvements in implantable defibrillators, including fibrillation detectors and high energy pulse generators with related electrode configurations, have been reported in the scientific literature and disclosed in patent publications.

Typically, electrodes for implantable defibrillators are made similarly to those developed for cardiac pacemakers, except defibrillation electrodes are larger than those used for cardiac pacing because a greater area of the heart tissue needs to be stimulated. These electrodes may be in the form of patches applied directly to the heart. The most common approach in the past has been to suture two patches to the epicardial tissue via thoracotomy. It has been theorized that electrodes with large surface areas are important for a wider distribution of current flow and a more uniform voltage gradient over the ventricles. Others have postulated that uniformity of current density is important since: (i) low gradient areas contribute to the continuation or reinitiation of ventricular fibrillation, and (ii) high current areas may induce temporary damage, that then may cause sensing difficulties, set-up areas of reinitiation of fibrillation, or even potentially cause permanent damage (new arrhythmias, decreased contractility, and myocardial necrosis).

For most patients, the best conventional devices and implantation methods are those that avoid surgical entry into the chest cavity and attachment of epicardial electrodes. Employing a less invasive surgical technique, one or more defibrillation electrodes are implanted proximate the pleural cavity and rib cage, and are used in combination with one or more coil electrodes positioned in the right atrium or right ventricle of the heart. This kind of defibrillator is described in U.S. Pat. No. 5,203,348, issued to Dahl, et al.

Stimulation of tissues requires that the charge be injected reversibly by a purely capacitive mechanism. In such a mechanism, the electrode behaves as a charge flow transducer whereby electrical discharge takes place in a unidirectional manner between media exhibiting different charge flow properties. The capacitive mechanism allows electrons to flow away from the stimulation electrode causing electrical charges at the electrode/electrolyte interface to orient themselves in order to cause a displacement current through the electrolyte. Since the electrolyte is an ionic medium, the slight displacement of the ions in reorientation creates a charge flow.

When irreversible chemical reactions begin to occur as a result of poor electrode selection or exceedingly high currents or other thermodynamic or kinetic limitations, the mechanism is no longer capacitive. Irreversible faradaic reactions may lead to water electrolysis, oxidation of soluble species, and metal dissolution from the electrode. In addition, some of the products of the reactions may be toxic. Neither gas evolution nor oxide formation reactions contribute to electrical stimulation of excitable tissue and stimulation energy is wasted in electrolyzing the aqueous phase of blood instead of carrying desirable charged species from one electrode to the other via the tissues. Because of the need for high energies in defibrillating the heart, higher currents are usually generated from the defibrillator than from a pacemaker. Under such circumstances, the efficiency of the electrode during high current generation is vital in not only reducing the defibrillation threshold, but in reducing the unwanted gas reactions or oxide formation. Excessive levels of gassing reactions may also lead to embolism in other vital organs such as the brain. Thus, stimulation electrodes should preferably allow a large charge flow across the electrode-tissue interface without the risk of irreversible faradaic reactions. Selection and design of the metal of the electrode is critical.

A metal of choice in electrode manufacturing has traditionally been titanium. On a fresh titanium surface, however, oxygen ions react with the titanium anode to form an oxide layer. Once a finite oxide thickness has been formed on the surface, polarization increases further. A point is reached when the oxygen ions reaching the surface of the titanium cannot be reduced further to form the oxide, and instead are reduced to elemental oxygen to form oxygen gas. The oxide film developed on the surface of a titanium electrode, either naturally or electrochemically, is irreversible. It cannot be reduced to the original metal by passing a charge in the reverse direction. Hence, it is clear that virgin titanium metal is a poor choice for electrode construction, since it forms a semi-conductive oxide on its surface before and even during the electrical stimulation. Platinum, and much more so stainless steel, have been shown to undergo irreversible dissolution during stimulation as well.

Very recently, the "hot can" type of implantable defibrillator has come into wide use. In this type of defibrillator, one of the defibrillation electrodes is formed by the stimulator housing itself, or a face, window or portion thereof. The unit is placed subcutaneously or extra-pericardially, such that the shock current will flow through the ventricular septum to a transvenous lead placed inside the heart. An example of this kind of defibrillator is described in U.S. Pat. No. 5,480,416 issued to Garcia et al.

Conventional titanium hot can electrodes, by their failure to be essentially reversible in redox reaction along their surfaces, permit build up of the irreversible electrochemical products upon the surfaces. This results in entrapment of ions, molecules, etc. derived from the serum or body tissue in closest contact with the electrode surface, such as chronic coagulation and fibrotic growth. This in turn results in a greater likelihood of coagulation of blood, fibrin formation and other clotting cascade moieties immediately next to the surface or entrapped therein. These entrapped and surface blocking particles further reduce the ability of the surface to pass a charge and lead to increased impedance across the electrode surface.

Titanium oxidation reactions are several times more likely in an oxidative environment than those of platinum or platinum alloys, but a thousand times less so than those of stainless steel. Unfortunately, due to the expense of platinum metal and the requirement for large amounts of metal in patch-type electrodes, production costs are too high for platinum electrodes. Because of the low current requirements for pacemaker electrodes, the need for high surface area may not be too critical. However, it becomes crucial to implement a high surface area electrode with low polarization so as not to cause too much gassing reactions. At this time, platinum is generally used only in pacemaker electrodes and transvenous defibrillation electrodes, and not in hot cans. The use of platinum in transvenous defibrillation electrode is either in the form of a planar, low surface area alloy as platinum/iridium, or as a smooth, low surface area platinum coating on a titanium substrate. In such latter cases, the use of maximizing the surface area by making the platinum porous is usually avoided because of the possibility of increased clotting on a porous surface. However, this exposes the possibility of increased current density and increased gassing reaction which may lead to possible embolism. Thus, even though oxidation problems are more prevalent in them, titanium is typically used for conventional pacing and defibrillator electrodes as the substrate material.

U.S. Pat. No. 5,601,607, issued to Adams, also discusses the problem with achieving optimal electrode function with conventional hot can, also called "active can," electrode designs due to oxidation of the can material, particularly with cans made of titanium or stainless steel. The '607 patent addresses the problem by coating the can with a noble metal, such as platinum, to reduce the effects of oxidation on the can material over multiple shocks.

A problem that is still not widely recognized at this time by those working in the area of cardiac stimulators, however, is that the housing ("can") material becomes porous as increasing numbers of shocks are administered, particularly with conventional titanium cans. As a result, the interfacial contact between the can surface and the body tissue diminishes and the path for adequate delivery of ionic current is correspondingly reduced, as illustrated in FIGS. 1A–B, and discussed in the Detailed Description, below. This results in high polarization at the can/tissue interface and leads to unacceptably high levels of defibrillation thresholds (DFTs).

In order to avoid passivation on the surface of titanium pacer electrodes, an iridium oxide ("IrOx") coating has been employed on the electrode of a pacing lead, as disclosed in U.S. Pat. No. 4,919,135 (Phillips, Jr. et al.), issued to Intermedics, Inc. The oxide formed by iridium is very stable, does not grow further, and is electrically conductive. In addition, it provides protection for the underlying metal and is reversible to aqueous based redox species, undergoing reversible redox reactions with species such as hydrogen ions and hydroxyl ions, leading to the formation of higher oxidation state surface oxides. U.S. Pat. Nos. 4,717,581 and 4,677,989 teach deposition of iridium oxide onto the metal surface of an electrode. IrOx is rough, however, and it has been observed that rough-surfaced electrodes usually tend to cause scar tissue formation. In a surprising finding using the electrodes of the invention, it was found that the electrodes are capable of reducing the amount of both acute and chronic coagulation of blood surrounding the electrode. It is postulated that this reduction in the amount of coagulation of blood is a direct result of the reversible reduction-oxidation occurring over the enhanced electrically-accessible area of the electrodes. Where coagulation occurs immediately upon placement of the electrode in the tissue, it is said to be acute. Certain prior art electrodes have failed to be essentially reversible in redox reaction along their surfaces where the build up of the irreversible electrochemical products upon the surface results in entrapment of ions, molecules, etc. derived from the serum or tissue in closest contact with the electrode surface (chronic coagulation, fibrotic growth). This in turn results in a greater likelihood of coagulation of blood, fibrin formation and other clotting cascade moieties immediately next to the surface or entrapped therein. IrOx coated electrodes have not been employed for hot can electrodes.

An electrically stable can material that does not form an oxide in situ when subjected to numerous shocks, and provides a large charge flow, is needed for construction of the hot can defibrillator electrode. Such a material should also be very conductive and provide a very good tissue/can interface. An ideal electrode with a large charge flow can be obtained by selecting materials that: (a) are electrically stable; (b) undergo reduced unwanted reactions such as oxide formation or gassing reactions; (c) reversible; (d) reduce inflammation of the adjacent tissue and hence, provide thinner fibrous capsule at the electrode/tissue interface; (e) provide a continuum electrical interface with the tissue and electrode; and (f) are designed for high surface area. It would be beneficial to have a hot can defibrillator electrode that maintains a uniform defibrillation threshold over the useful lifetime of the unit.

BRIEF SUMMARY OF THE INVENTION

The compositions, apparatus and methods of the present invention provide a way to remedy some of the disadvantages of conventional hot can defibrillator electrodes by coating the housing ("can") of an implantable cardiac stimulator with material that maintains a surface that is stable and does not undergo significant change during repetitive shocks over the lifetime of the device. The new ionically conductive polymer coatings provide a corrosion resistant barrier for the metal housing and the ionic carrier itself is able to undergo reversible redox reactions. The reversible redox capabilities of the ionic carrier is desirable so as to prevent a continuous build-up of species such as irreversible oxides or other compounds that may degrade undesirably over time and could lead to poor transport barriers and high impedance at the can/tissue interface. The use of coatings such as IrOx that provides a structure for reversible ion transport helps to avoid such problems associated with build-up of undesirable species. In addition, the reversible characteristic provides added redox capacity to the charge stimulation which aids in reducing the current density and distribution of charge over a large surface area, minimizing tissue ingrowth and tissue irritations as well as reducing gassing reactions that may lead to embolism. Plain titanium electrodes behave in the opposite manner to IrOx coated titanium electrodes.

Also comprehended by the present invention is a method of making an electrode having a roughened, or porous, platinum surface over a titanium substrate, and an ionically conductive polymer coating filling in the pits and crevices of the platinum surface to retain the effective high conductive surface area while providing a smooth, flat tissue/can interface. Advantages of employing a hot can having the new enhanced surface/polymer coated electrode, compared to conventional titanium cans, arise from having better interfacial contact between the polymer/platinum and the tissue. Therefore, the loss of energy that would otherwise take place due to poor interfacial conductivity is minimized. This additionally results in low polarization characteristics, as impedance that typically results from voids in a dry pocket or voids due to the porous electrode can is reduced with the hot cans prepared as described herein.

Since the platinum layer of certain preferred embodiments of the present invention is applied as a very thin layer on the etched titanium, the resulting electrode's surface roughness is still appreciable. In order to maximize electrode performance, a polymeric coating is then applied to the platinum so that the outer surface is fairly smooth. A smooth surface optimizes the interface between the electrode and the fibrous capsule which almost always develops in vivo over a period of time. During implantation, injection of saline within the fibrous pocket allows the saline to absorb into the polymer and enhance and maintain a very good ionically conducting interface, thereby eliminating the dry pocket syndrome which otherwise results on a porous electrode surface. Use of a cardiac stimulus generator having the smooth polymeric interface of the present invention will result in a thinner fibrous capsule formation and enhances the opportunity for blood channel development between the electrode and the bulk of the tissues. This, in turn, will allow more efficient conduction to the right ventricular ("RV") electrode.

The hot can electrode of the present invention is able to undergo essentially freely and completely reversible reduction-oxidation across the surface of the electrode. Since this renewal process is reinitiated upon each pulse or charge delivery, there is a much greater active surface life for the hot can electrode of the invention over those previously known. Although preferred embodiments of the invention describe a "hot can" type of electrode, the coatings and methods of the present invention may also be used to make any other stimulus electrode with a porous structure, such as RV and superior vena cava ("SVC") electrodes.

In accordance with the present invention, an ionically conductive polymeric composition for coating an implantable cardiac stimulus electrode is provided. The composition comprises a polymer such as polyethylene oxide, polyethylene terpthalate, a hydrogel or a polyacrylate, mixed together with an ionic medium such as NaCl. The molecular weight of the polymer is large enough to avoid solubilization of the polymer or the ionic medium when an electrode coated with the polymer composition is used in the body for delivering electrical pulses. Preferably the molecular weight is about 100,000 to 10,000,000 daltons, and more preferably between 100,000 to 5,000,000. The preferred ionic medium is NaCl, but other similarly ionizable compounds may be substituted, as long as it does not significantly alter the recipient's body chemistry during the period of time that the coated device will be in place. In some embodiments, the polymeric composition also includes a steroid and/or an inorganic filler material. In other embodiments, the polymeric coating includes an antithrombotic, anticoagulant, antiseptic or anti-infectant or a thrombolytic agent to enhance the efficiency of the unit in situ or to provide other localized beneficial medicaments in long-lasting form.

Another embodiment of the invention provides an electrode for a cardiac stimulator. The electrode comprises a titanium substrate that has a porous surface structure, and that is electrically connected to a stimulus generator. Minimally coating the porous structure is a layer of an oxidation resistant metal. The metal coated porous structure is filled with an electrically conductive polymeric coating and the polymeric coating also forms a smooth outer surface on the electrode. The metal that is used to coat the porous structure is platinum, ruthenium, rhodium, palladium, osmium, iridium or an alloy of those metals.

An alternative embodiment of the invention provides an electrode for a cardiac stimulator that has a titanium substrate with a porous electrically-conductive metal or metal oxide layer deposited on top of the titanium substrate to form a porous layer. Coating and permeating the porous layer is an electrically conductive polymeric coating which provides a smooth outer surface on electrode. The deposited porous layer may be platinum black, or it may be a metal oxide of platinum, ruthenium, rhodium, palladium, osmium or iridium. In certain embodiments, the porous layer is IrOx.

Also provided by the present invention is an implantable cardiac stimulator comprising an electrical stimulus generator capable of delivering a defibrillation shock and having a housing that encloses the stimulus generator. At least a portion of the housing serves as a first electrode, which is electrically connected to the stimulus generator. The first electrode includes a substrate, such as titanium, that has a porous surface, and the first electrode also includes an outer surface. A second electrode is also electrically connected to the stimulus generator, and this second electrode is adapted for placement inside the heart. The second electrode and the first electrode cooperate with the stimulus generator in delivering defibrillation shocks to the heart. In this embodiment, a layer of oxidation resistant metal minimally covers the pores of the first electrode and an electrically conductive polymeric coating permeates the metal-covered pores and forms the smooth outer surface of the first electrode. In some embodiments, the cardiac stimulator also has an electrically insulative coating with a window in the coating.

In still another embodiment of the present invention, a method of making an implantable cardiac stimulator is provided. The method includes removing entrapped gas from the porous surface of a stimulator housing, at least a portion of the housing forming an electrode with a porous-surfaced metal substrate. The pores are then impregnated with a solution comprising a biocompatible polymer, and a biocompatible ionic carrier, followed by evaporation of the solvent from the impregnated surface. A smooth polymeric outer surface is thereby formed on the electrode. Suitable polymers include polyethylene oxide, polyethylene terpthalate, polyacrylates, and the like. Impregnation of the pores can be accomplished by soaking or ultrasonicating the porous surface in a solution of 5–10% polyethylene oxide and 1–2% NaCl in alcohol.

Another embodiment of the invention is an improved method of making an implantable cardiac stimulator of the "hot can" type, having a titanium housing. The new method provides for applying a porous coating of a noble metal or an oxide thereof, such as platinum or iridium oxide. The porous coating may also be platinum, ruthenium, rhodium, palladium, osmium, iridium, or an oxide thereof. An ionically conductive biocompatible polymer, which is capable of reversible reduction-oxidation, is applied to the porous coating such that it permeates and covers the porous coat and forms a smooth outer surface on the electrode.

In an alternative embodiment, an improved method is provided for making an implantable cardiac stimulator having a titanium housing comprising one of the stimulation electrodes, wherein the "hot can" electrode has a porous structured surface. A coating of a metal such as platinum, ruthenium, rhodium, palladium, osmium and iridium is applied to the porous electrode surface is such a way that the metal coating essentially conforms to and retains the porous structure. To the metal-coated porous electrode, an ionically conductive biocompatible polymer capable of reversible reduction-oxidation is applied so as to fill and cover the porous structured electrode, whereby a smooth outer surface is formed. This surface is then coated with an ionically conductive polymeric material coating and filling the pores of the electrode. Preferably, the coating material is biocompatible, chemically and mechanically stable over several years and does not dissolve or leach out over time. The outer surface of the preferred electrode of the present invention preferably includes a smooth coating of the conductive material so that the interface with the tissue is complete, permitting the entire surface area of the electrode to be utilized and eliminating voids that would otherwise cause the DFT to increase with time and use.

One embodiment of the present invention provides an ionically conductive polymeric material for coating an implantable porous metal or metal oxide electrode, the polymeric material containing a polymer and an ionic medium, or electrically conductive carrier, admixed therewith. The polymer preferably has a molecular weight large enough to avoid solubilization or leaching of the polymer or the ionic medium when an electrode coated with the polymeric material is used for its intended purpose, such as for delivering a defibrillation shock to the heart. The polymeric material may be polyethylene oxide, polyethylene terpthalate, polyacrylates, or other suitable polymeric hosts that satisfies the need as a biocompatible medium capable of maintaining an ionic carrier within the polymeric matrix. The ionic carrier may be NaCl, or another similarly ionizable compound that is biocompatible with the body and does not significantly alter the body chemistry over long periods of time.

Another embodiment of the present invention provides an implantable cardiac stimulator having an electrical stimulus generator capable of delivering a defibrillation shock. The housing enclosing the stimulus generator has at least a portion of its outer surface serving as an electrode in electrical communication with the stimulus generator, and has an electrically conductive polymeric coating on at least that portion of the housing that serves as the electrode. The defibrillator also has a second electrode that is electrically connected to the stimulus generator and is made to be placed in direct contact with the heart, by routing through an artery, for example. This second electrode is capable of cooperating with the can electrode on the stimulus generator housing to deliver a defibrillation shock to the heart, when needed. The conductive polymeric coating on the outside of the housing preferably deters oxidation of the metal or metal oxide surface of the housing, even when the outer surface of the housing is a porous metal oxide, and the ionically conductive coating itself is oxidation resistant. Preferably, the defibrillator is adapted for implantation pectorally.

In certain preferred embodiments of the defibrillator of the present invention, the housing is titanium and the outer surface, or a part or area thereof, has a first coating of IrOx or another surface enhanced platinum or other noble metal, or oxide of such metal. This first coating is permeated and covered by an electroconductive polymeric coating such as polyethylene oxide having a molecular weight of about 100,000 to 5,000,000 daltons.

The present invention also provides a method of making the defibrillator described above. The method includes removing entrapped gas from the porous surface of the housing, impregnating the porous surface with a solution comprising 5–10% polyethylene oxide and 1–2% NaCl in a suitable solvent such as alcohol, and evaporating the alcohol from the impregnated surface to form a stable coating throughout and on top of the porous layer. The porous layer may be saturated with the electroconductive polymeric solution by soaking or untrasonicating the apparatus so as to completely fill or wick the porous body, or the porous layer may be soaked with a precursor polymer solution and radiation, heat or chemically cured subsequently yielding the same result.

The present invention also provides an improved method of making an implantable cardiac defibrillator having a housing comprising one of the electrodes, said electrode having a metal or metal oxide surface, wherein the improvement consists of coating the surface with an electrically conductive polymer capable of reversible reduction-oxidation.

These and other objects, features and advantages of the present invention will become apparent with reference to the following description and drawings.

BRIEF DESCRIPTION OF THE SEVERAL VIEWS OF THE DRAWING

For a detailed description of a preferred embodiment of the invention, reference will now be made to the accompanying drawings wherein.

DETAILED DESCRIPTION OF THE INVENTION

It has been observed that one of the major requirements for a high performance porous stimulation electrode is that the electrode have a high surface area that will result in a large capacitive discharge. The effectiveness of the electrode's surface area can only be fully utilized, however, if (1) all the pores in the electrode can be made accessible to the conducting fluid (the blood, for example) and (2) if this fluid is sufficiently conductive to transmit the ionic discharge from the intrinsic surface of the electrode, to the myocardial tissue or other tissue to depolarize the cells. The intrinsic surface of the electrode includes the surface area of all of the micropores from the electrode substrate to the outer electrode/tissue interface. Requirements (1) and (2) are usually met in cases where the electrode is implanted within the heart or in the veins (e.g. SVC or innominate vein), where the intrinsic surface can readily be wetted by blood. However, in some cases where gross fibrosis occurs, proper wetting is no longer achieved and high resistance gas or "air" pockets within the pores may develop as a result of gases evolving at the electrode. The presence of these gas pockets reduces the availability of conductive channels within the porous electrode structure. As the use of the hot can becomes the norm, with the can being implanted pectorally in a usually dry pocket, the problem of inadequate wetting will become more common. A "dry pocket" refers to a situation in which the fibrous connective tissue is in poor contact with the hot can electrode and additionally is dry and thick with little blood channels to the electrode that would otherwise provide good ionically conducting pathways for the charge to flow from the electrode to the counter electrode placed in the right ventricle. A dry pocket will lead to air pockets at the can/tissue interface as well as in the pores of the electrode surface. Because of this, in many situations, electrodes with a planar surface design will tend to defibrillate a lower energy level than those with a porous electrode structure irrespective of the type of material for the porous structure. Conversely, a "wet" pocket will usually be a thinner fibrous connective tissue and will always have a good wet interface between the inner linings of the fibrous capsule and the electrode. This arrangement ensures a good ionically conductive pathway for the charge to flow from the electrode surface to the counter electrode. In addition, a wet pocket will also tend to wet the electrode surface which may be the polymeric coating improvement in this invention or the IrOx or other metal or metal oxide surface.

Figure 1A:
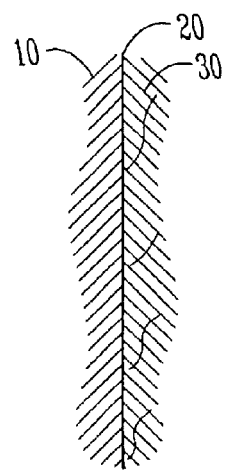
FIG. 1A is a detail drawing of a tissue-to-can interface with a conventional titanium hot can electrode, prior to administration of any shocks.
Figure 1B:
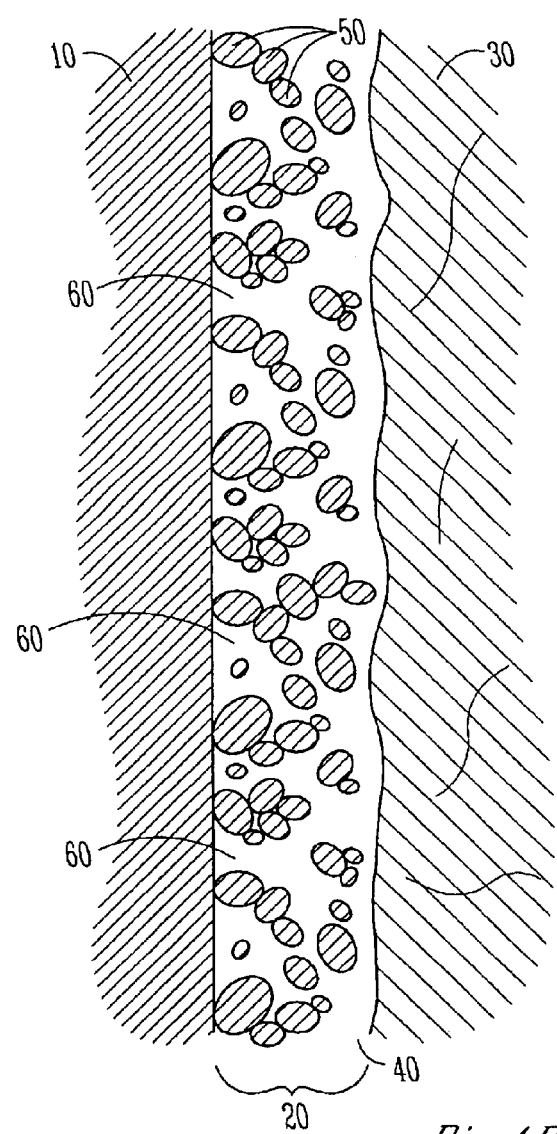
FIG. 1B is a detail drawing showing the altered interface of the electrode of FIG. 1A after several shocks.

As a result of implantation in a dry pocket, the interfacial contact between the can surface and the tissue diminishes and hence the path for adequate delivery of ionic current is also reduced. This results in high polarization at the can/tissue interface and leads to high defibrillation thresholds. FIGS. 1A–B illustrate this problem, both before a shock is administered between the can and the opposite electrode (FIG. 1A) and after several shocks (FIG. 1B). The interface 20 of the titanium housing 10 with adjacent body tissue 30 is initially close and continuous along the can surface, providing good electrical contact for administration of shocks (FIG. 1A). As more shocks are delivered through the can electrode, oxide growth 50 increases, resulting in a porous structure 40 at interface 20 (FIG. 1B). This is true when, for example, titanium serves as the can material, forming TiO and becoming more porous as successive shocks are given to the patient. Porous structure 40 is not easily wetted because of the dry pocket environment, leading to high resistance gas pockets (not shown) in pores 60 and hence high levels of polarization. Because of the high impedance developed, this polarization is wasted energy mostly in the form of gassing reactions at sites where the first level of ionic conduction could take place at the electrode, usually in sparsely wetted areas. Gassing reactions would further deplete the sparse reservoir of bodily fluid at the electrode and result in even higher impedance and greater polarization with time eventually leading to a possible fatal situation where the energy level to defibrillate the heart exceeds what the defibrillator can provide. Other disadvantages of high levels of polarization and gassing reactions include possible embolism. Hence, it is imperative for the safety of the patient that the electrodes are designed with improved performance.

This detrimental result from using a porous electrode contrasts with what is more commonly the case (i.e., when a pacing electrode is placed in a wet environment), where a porous structure serves to enhance conduction by increasing the effective conductive surface area. Conventional stimulus electrode design has drawn for the most part from experience with wet pocket situations. In the following examples, ways are described to overcome problems associated with porous electrodes and how the use of porous can surfaces as electrodes could be made to be beneficial, even in dry pockets.

The following examples are offered by way of illustration and are not intended to limit the scope of the invention in any manner. All of the materials used in these examples are readily obtainable from well known commercial sources, or as specifically stated in the examples.

EXAMPLE 1

Ionically Conductive Polymer Coating Over a Platinum Coated Can

For conventional titanium cans, one way to rectify at least some of the above-described problems is to coat the titanium can with a material that is stable and does not undergo any change as a result of the shocks during the lifetime of the device. A "stable" electrode must be electrically stable such that the electrical impedance does not change with either time or current passage. The electrode material must be biocompatible and must not react with the bodily fluid passively. Yet another criteria for stability is that the electrode material must not undergo irreversible oxidation-reduction reactions such as in the case of a titanium electrode forming titanium oxide with the passage of current. The material must not dissolve with the passage of current. The material must have good mechanical integrity and must not change shape or slough with attrition or usage in the body. A smooth platinum coating over the titanium substrate provides such an electrode.

As previously mentioned in the Background of the Invention, U.S. Pat. No. 5,601,607 issued to Adams, describes a platinum coated titanium can and teaches certain advantages of placing a stable, noble coating over the titanium of conventional cans. The '607 Patent discloses that the platinum or other noble metal coating provides a corrosion/oxidation resistant surface for an active can electrode. The need for coating the can with a stable material was not apparent in the past because (1) in the case of the pacemaker, where the can in some instances served as a counter electrode, the current levels were several orders of magnitude lower than that of the defibrillator, and therefore low levels of current did not create a very large surface texture, and (2) the "hot can" or "active can" type of defibrillator that is now widely practiced is a relatively new concept, and problems associated with its use have not yet emerged or have not yet been widely experienced in the field. In addition to the problem of corrosion/oxidation of conventional titanium electrodes in the body, there is the further problem of deteriorating tissue-to-electrode surface interface with repeated shock delivery. One disadvantage of in vivo use of a titanium electrode having a smooth platinum coating is that there is less total surface area compared to high surface area porous titanium electrodes. In addition, there is the disadvantage of increased possibility of developing higher current densities at the can/tissue interface, with repeated use. This can lead to poor efficiency in the charge transfer, and hence to higher levels of polarization and gassing reactions, which, in turn, can lead to physiological problems. Higher currents at the tissues are undesirable because of the possibility of tissue burning locally and causing increased generation of dead tissue at the interfacial sites. It can readily be seen how an undesirable chain of events can occur with use of an electrode that develops high current densities at its tissue interface.

Because this latter problem is not generally recognized at the present time, there is a paucity of solutions for the problem. The '607 patent, for instance, does not address this additional need for an implanted can to maintain a high surface area electrode and a good can/tissue interface.

Figure 2A:
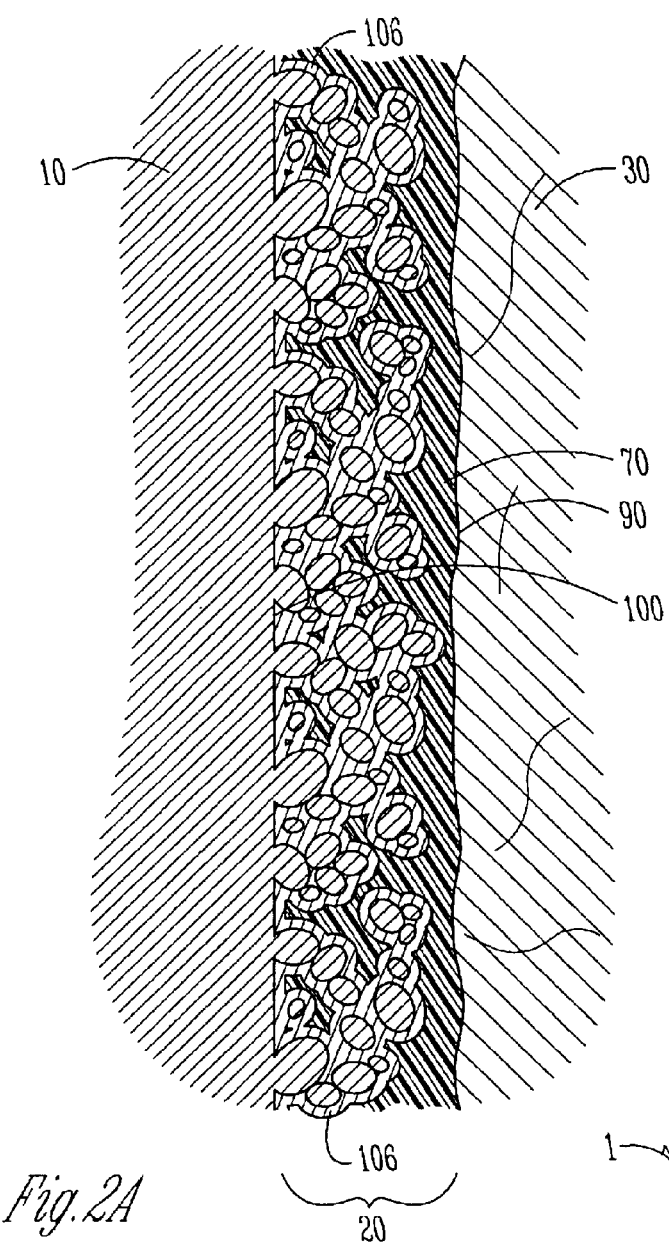
FIG. 2A shows a cross-sectional view of the tissue/can interface a can produced in accordance with the present invention, having a porous surfaced electrode, a noble metal coating and the polymeric coating of the present invention.
Figure 2B:
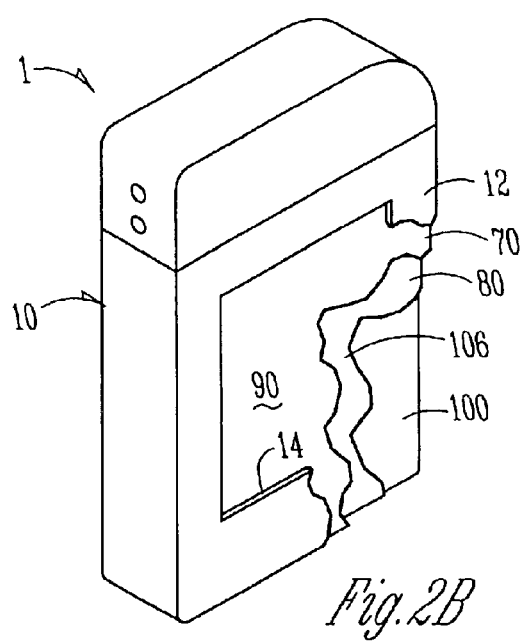
FIG. 2B shows, in partial cut-away view, a can produced in accordance with the present invention, having a porous noble metal or metal oxide surface and the polymeric coating of the present invention.

An improvement over known titanium electrodes, including "hot can" electrodes such as that disclosed in the '607 patent, is provided by the present invention by increasing the effective surface area of the electrode, overlaying this roughened, or enhanced, substrate with a thin coating comprising a conductive polymer. FIG. 2B illustrates, in partial cut-away, view of the tissue/can interface of a polymer coated can 1 in accordance with the present invention. A conventional defibrillator unit 1, having a titanium housing 10 coated with an insulative material 12, such as parylene, and an uncoated area or window 14 in coating 12, includes an etched, or otherwise surface area enhanced, titanium surface 100 that functions as one of the stimulus electrodes. Over titanium surface 100 is a high surface area noble metal layer 106. Permeating and overlying noble metal layer 106 is a conductive polymeric coating 70 that has a smooth outer surface 90, as best show in enlarged detail in FIG. 2A. The coated unit is prepared as follows. First, the surface area is increased by highly etching the titanium can surface with acid, such as oxalic acid at 80EC for one to two hours, as previously described in U.S. Pat. No. 5,645,030 ("the '030 patent") for transvenous electrodes, the disclosure of which is incorporated herein by reference. In this way, the surface area of the substrate is increased by as much as 20 times over the planar surface area of the original can. Next, a very thin stable coating of electrode material, such as platinum, is deposited on the etched substrate in such a way that the platinum layer literally follows the contours of the etched pattern, or porous structure. This is accomplished by ion beam deposition, sputtering, evaporation, plasma spraying, chemical methods, or other means. Care is taken to make the platinum layer continuous but not so thick that it fills in the voids, or completely blocks the etched pattern with the coating material. In this way a high surface area platinum is generated which retains a great deal of the original surface roughness. Although the preferred coating material is platinum, another similarly stable electrode material, such as ruthenium, rhodium, palladium, osmium, iridium, or an alloy of any of those metals, could be substituted with good results.

Figure 3A:
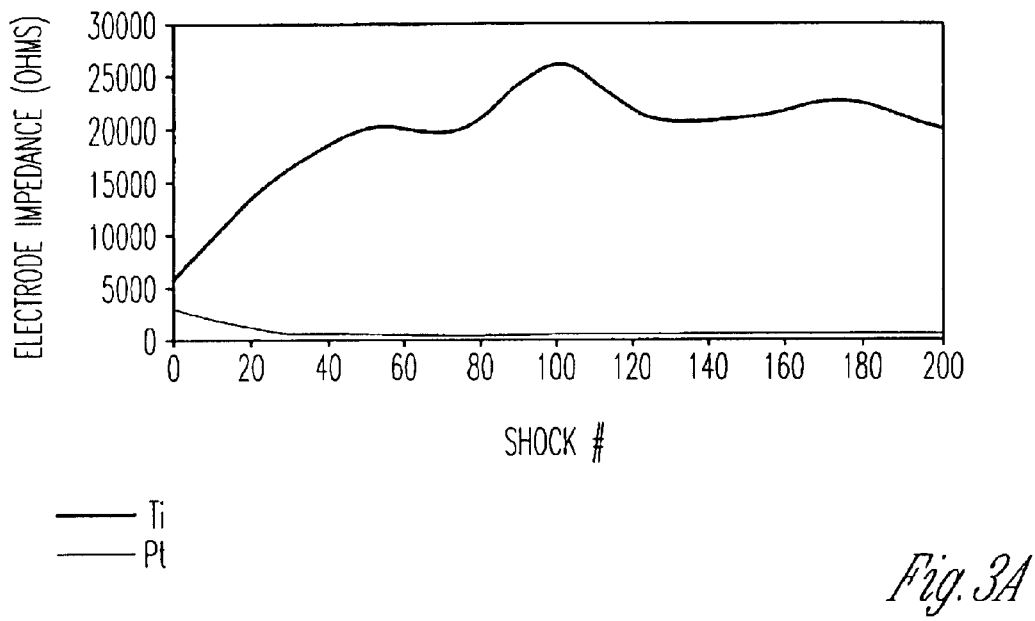
FIG. 3A is a graph showing electrode interfacial impedance as a function of number of shocks delivered for a bare titanium electrode and for a platinum coated titanium electrode.

Tables 1 and 2, and FIGS. 3A,B compare electrode interfacial impedance and polarization voltage, respectively, as a function of the number of shocks administered for a conventional titanium can and for a platinum coated titanium can in which the titanium was etched to increase its surface area, as described above. The platinum layer tested was about 0.1 F. thick and the titanium etched depth was about 5–10 microns. The entire surfaces of both the titanium can and the platinum coated titanium can served as the electrode. In Tables 1 and 2, electrical impedance and polarization shock voltages were measured in vitro as a function of shock number and the values were found to be close to their original values.

TABLE 1

Electrode Interfacial Impedance as a Function of No. of Shocks (30 Joules)

| Cumulative No. of Shocks | Electrode Impedance (Ohms) | | |
|---|---|---|---|
| | Ti | Pt | IrOx |
| 0 | 5750 | 2900 | 7000 |
| 25 | 15000 | 875 | 6500 |
| 50 | 20000 | 580 | 6000 |
| 75 | 20000 | 425 | 5900 |
| 100 | 26000 | 525 | 5900 |
| 125 | 21000 | 550 | 6000 |
| 150 | 21000 | 550 | 6100 |
| 175 | 22500 | 700 | 6000 |
| 200 | 20000 | 600 | 6000 |

TABLE 2

Polarization Voltage Variation with of No. of Shocks (30 Joules)

| Cumulative No. of Shocks | Polarization Voltage (mV) | | |
|---|---|---|---|
| | Ti | Pt | IrOx |
| 0 | 116 | 70 | 45 |
| 25 | 346 | 24 | 37 |
| 50 | 492 | 20 | 21 |
| 75 | 574 | 28 | 20 |
| 100 | 594 | 19 | 19 |
| 125 | 583 | 19 | 19 |
| 150 | 560 | 18 | 22 |
| 175 | 509 | 17 | 21 |
| 200 | 498 | 17 | 21 |

In the examples shown, electrical impedance and polarization shock voltages were measured as a function of shock number and it was found that the values were close to their original values.

Figure 3B:
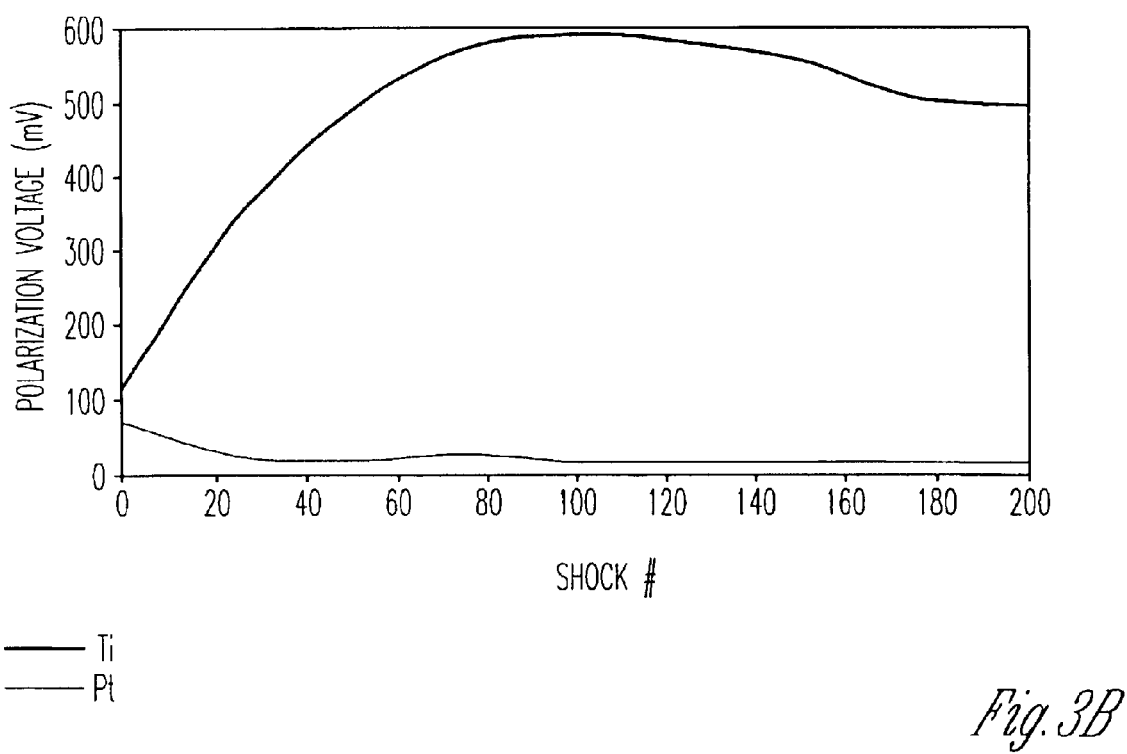
FIG. 3B is a graph showing polarization voltage as a function of number of shocks delivered for a bare titanium electrode and for a platinum coated titanium electrode.

FIGS. 3a and 3b depict the variation of electrode impedance versus shock number and polarization voltage versus shock number, respectively, for titanium and platinum coated titanium plates of area 84 square centimeters. The electrode impedance was measured in a 50:50 solution of Ringers lactate and deionized water containing the electrode under test, a calomel reference electrode and a platinum counter electrode. The impedance was measured using a potentiostat connected to a lock-in amplifier at frequencies between 100 Hertz and 100 KiloHertz. Values of electrode impedance in ohms were computed from the frequency response curves.

The polarization voltage was measured in the same solution using the same kind of electrode configuration but just using a potentiostat. Galvanostatic pulse of 2 mA were imposed on the test electrode and the instantaneous drop in voltage as measured against the reference electrode was measured. This was taken as the polarization voltage measured in millivolts. Both the impedance and polarization voltage were measured as a function of shock number. The shocks were provided by a in-house built shock box providing 30 Joules of biphasic shocks over 10 milliseconds from a bank of capacitors connected to a power supply. During the shocks, it was observed that titanium started to discolor from a greyish color to gold after a few shocks to purple after about 20 shocks to bluish white after 100 shocks. This phenomenon is the result of oxidation of the titanium and change in the valence state of the metal oxide from titanium three plus state to titanium four plus state. This resulted in a rise in the impedance of the titanium surface as well as resulting in a larger voltage drop with increasing number of shocks during the pulsing experiment.

On the other hand, there was no oxide or degradation reaction with platinum except electrolysis of water with shock number. As a result, platinum remained unchanged and in fact became reduced in impedance and polarization voltage. This may be due to surface improvements such as impurity removal, surface area enhancement as a result of the high voltage shocks, microstructural changes, or other phenomena.

If, however, the high surface area platinum coated can (at this point in the process) were used for implantation into a patient, and/or if a dry pocket or gross fibrous capsule were encountered, the effective surface area of the electrode would very likely decrease, blood clots could form, the current density at the electrode surface would be likely to increase and gassing reactions could occur. Such problems are minimized or avoided, however, by inclusion of a further processing step. The next step is to apply to the platinum layer a coating of an ionically conductive polymer such as polyethylene oxide doped with a sodium salt. The polymeric coating need not be thick, a coating that is just thick enough to permeate the pores and to provide good integrity without being subject to dissolving or peeling off the can is sufficient. The resulting coating has a smooth finish and provides a good can/tissue interface. A suitable polymer coating is described in more detail in the example which follows.

During implantation of the polymer/platinum coated device, the physician insures a wet pocket by injecting some saline into the pocket which will be absorbed by the polymer, and hence will provide an enhanced ionically conducting media. By using the improved platinum coated case described in this example, one obtains all the benefits of the platinum electrode while avoiding the likelihood of development of reduced electrode surface area. Additionally, the current density at the electrode surface is lowered and likelihood of gassing reactions and possible embolism are reduced. To insure even less tissue irritation by the implanted device, a steroid such as dexamethasone is absorbed into the polymer coating matrix. If a high molecular weight polymer is used, the chances of this steroid eluting too fast is very low, and instead, it can be expected to remain indefinitely within the polymer and prevent formation of a thick tissue capsule. A thinner capsule allows greater possibilities for blood vessels in the connective tissue ensuring improved ionic flow and low thresholds.

In an alternative method, porous platinum such as platinum black may be used on top of the titanium can instead of using the chemical etching treatment and platinum deposition described above, to produce the high surface area platinum coating. In this modification of the above process, a smooth layer of one or more species of platinum precursors are initially deposited on the metallic surface of the can by dipping the workpiece into a solution of platinum compounds, in accordance with well known chemical methods. A suitable platinum precursor compound is $H_2PtCl_6$. The platinum precursors are then heated at elevated temperatures sufficient to form the platinum black coating. When the enhanced platinum coating is to be applied to finished cans (such as those having electronics and/or power sources already encased in the defibrillator housing), however, it is usually too problematic to heat the platinum precursors at elevated temperatures sufficient to form the platinum black coating. In those instances, it is preferable to apply the thin platinum layer to the porous substrate by conventional ion beam deposition, sputtering, evaporation or plasma spraying. However, for other applications where high temperatures do not pose a problem, a platinum black first coating would work as well. It should also be noted that applying the polymeric coating directly onto a bare titanium electrode surface would not, however, prevent oxide build up. In fact, it could result in a worse situation than without a polymeric coating.

EXAMPLE 2

Ionically Conductive Polymer Coating of an IrOx Coated Can

A desirable conductive coating material should be smooth so that the contact surface between the hot can electrode and the tissue is maximized and stable, ensuring that a porous coating is not developed. As described above in Example 1, a high surface area platinum coating is one way to provide a smooth, stable can/tissue interface. In many implantable stimulus devices, a porous conductive oxide surface such as IrOx has been used on lead electrodes. It has not been known, however, to employ such a conductive noble metal oxide coating on a hot can electrode. The conventional rationale for using IrOx coated electrodes is discussed above in the Background of the Invention. Also, there are clear economic advantages to avoiding use of the pure noble metals as coatings. Typically, IrOx electrodes are used for dispensing stimuli in the F joule range (for pacing applications) rather than delivering shocks of far greater magnitude (approximately 30 joules for hot can defibrillators). However, most recently, transvenous defibrillation leads implanted in the right ventricle or superior vena cava now have IrOx coated titanium electrodes and since these leads are placed directly in the blood, the chances of a dry fibrous capsule around the electrode is minimal. This is clearly evident from the very low defibrillation thresholds of 5 to 15 Joules that are observed with these leads in clinical usage.

Figure 4:
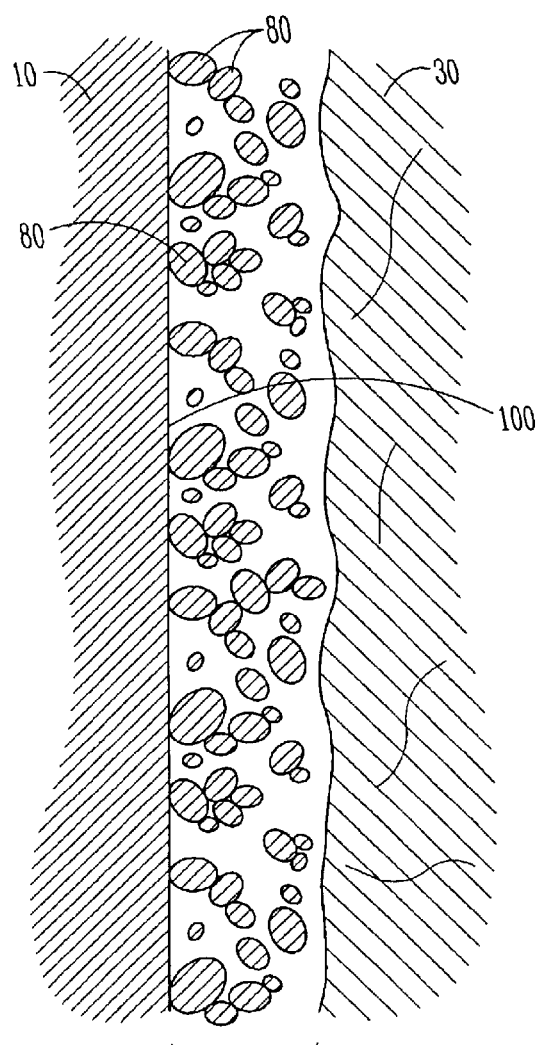
FIG. 4 is a detail illustration showing pores in the IrOx layer of an electrode, where high resistance gas pockets may form as a result of shocks and fibrous capsule formation.

FIG. 4 is an enlarged detailed illustration fo the can/tissue interface with a conventional IrOx coat 80 adheres to the surface of the titanium housing 10, making up interface 20 between the titanium surface 100 and the adjacent body tissue 30. For porous can surfaces such as a titanium can coated with an oxide such as IrOx, problems of poor interfacial contact with the tissue will occur, similar to the situation for bare titanium cans after repeated shocks. To address this problem, the conductive polymeric coating of the present invention was devised for filing the interstices of the IrOx coating and providing a smooth tissue interface. FIG. 2B illustrates, in partial cut-away, a can 1 produced in accordance with the 80 and the polymeric coating 70 of the present invention.

First, an IrOx coated titanium can is constructed by etching the titanium can halves in 10% oxalic acid solution at 80EC for about one hour according to procedures described in U.S. Pat. No. 5,654,030. The can halves are then washed and ultrasonicated in deionized water and the surface neutralized from the acid with a 5% sodium bicarbonate solution and washed in deionized water again. The defibrillator components are then incorporated into the two halves of the can before the halves are hermetically sealed by laser welding. The IrOx coating is applied either before or after can assembly, as desired. If it is before, a chemical or physical vapor deposition (PVD) process is used. If the IrOx coating is applied after the can has been assembled, then only the physical vapor deposition process is used, since in the chemical process the precursor material needs to be decomposed in order to convert the iridium material to the oxide at about 350EC. Most stimulus generator components cannot withstand the exposure to the required high temperature, which prohibits using this process for most applications. However, other ways of depositing the IrOx, such as plasma spraying may be also be used to deposit the IrOx successfully, without relying on PVD. During the deposition process, parts of the can are masked, as desired, to provide electrode windows for improved current delivery and current vectorization.

Following, IrOx coating, the can is coated with an ionically conductive polyethylene oxide polymer. This may be done simply by dipping the can in a solution containing 5–10% (w/v) solution of polyethylene oxide (PEO) (Aldrich Chemicals, Milwaukee, Wis.), molecular weight ranging from about 100 kd to about 5,000 kd, and about 1–2% (w/v) NaCl prepared in 50:50 (v/v) ethanol/water. Another alcohol such as isopropanol or any other similar alcohol, or other biocompatible solvent may also be used, provided that it is capable of dissolving the polymer and salt. The water-tight IrOx coated titanium can is soaked for about 5 to 10 minutes in the PEO/NaCl solution, under reduced atmospheric pressure sufficient to remove the entrapped gas from the porous surface, thereby permitting the solution to completely permeate the IrOx pores. Alternatively, the submerged can and PEO/NaCl solution may be subjected to ultrasonication for 5 to 10 minutes. The alcohol and water are then evaporated, preferably under reduced atmospheric pressure to allow formation of a stable coating, preferably about level with the outermost surface of the oxide layer. The final polymer coating is preferably about 2 to 10 microns in thickness and forms a smooth surface on the outer surface of the IrOx coat.

Although PEO is used in this example, if desired, one could easily substitute another polymer that can be made ionically conductive, is tolerated internally by the body and is chemically and mechanically stable over several years. Some suitable alternative polymers are hydrogels, acrylates and polyethylene terphthalates and modifications of these polymers. In some cases, it may be desirable to include a plasticizer such as more oligomers than monomers, or plasticizer salts to maintain the flexible character of the polymer for providing a better interface with the tissue. Likewise, another ionic carrier could be substituted for NaCl, if desired, as long as the resulting conductive polymeric material is biocompatible, is not subject to chemically or mechanically breaking down under internal use conditions, and does not dissolve or leach out over time. Monovalent ions such as sodium and potassium are preferable as the ionic carrier, although divalent ions such as magnesium and calcium could also be used, but their mobilities will generally be lower than the monovalent carriers. The coating material should be such that the polymer/ionic carrier solution wets all pores of the electrode, resulting in a continuous ionic network from the oxide or electrode interface to the tissue. After drying, the outer surface of the electrode is then a smooth coating of the polymeric material that provides an efficient, continuous interface with the tissue. In this manner, the complete surface area of the electrode is utilized and no voids are produced that would otherwise cause the DFT to increase.

Figure 5:
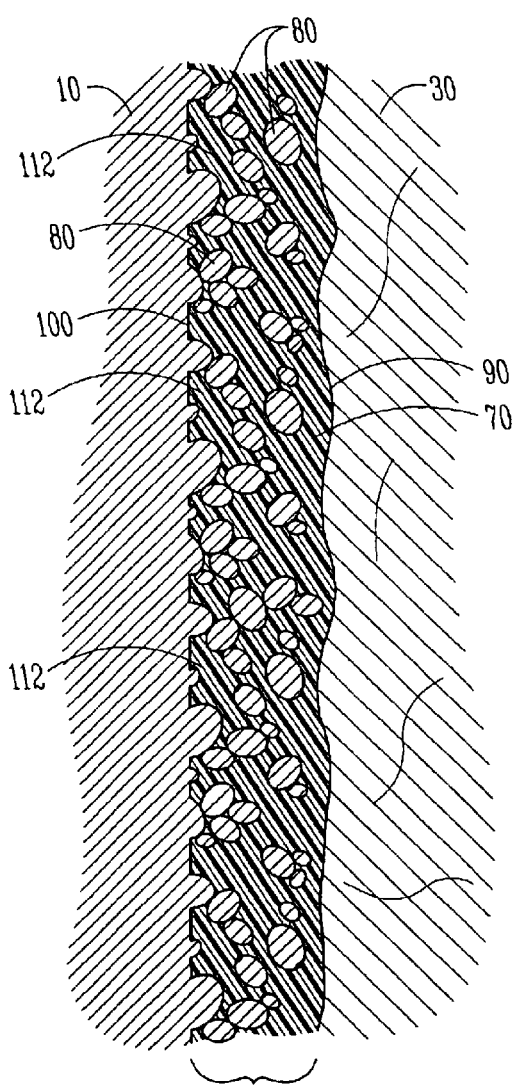
FIG. 5 is a detail drawing showing the tissue/can interface of a conductive polymer coating of the present invention, permeating the porous structure of a rough-surfaced hot can electrode and forming a smooth outer layer.

FIG. 5 is an enlarged detailed illustration of the tissue/polymer coated IrOx interface, showing how stabilization of the defibrillation threshold is accomplished. The polymer forms a smooth surface which comes into contact with the tissue, and also conforms to the contours of the IrOx on the surface as well as in the pores of the electrode. In the body, the polymer-coating of the IrOx electrode absorbs body fluids which are retained within the polymer. The ionic conductivity and mobility of the ionic carriers within the polymer matrix is thereby enhanced.

Coating the pores and surfaces with a polymeric type material such as an ionically conducting polyethylene oxide provides the improved effect of lowering the DFT, since the complete surface area of the IrOx coating is being utilized by virtue of making the internal porous surface accessible to the tissue. Although IrOx is a preferred first coating material, other porous materials such as those described in U.S. Pat. No. 5,654,030 may be substituted as the porous layer upon which the polymeric material is applied, to provide a satisfactory stimulus electrode.

TABLE 3

Defibrillation Energy Levels for IrOx Coated Ti Cans
in Canine Simulating Wet and Dry Pockets*

|  | Defibrillation Energy (Joules) |
|---|---|
| IrOx (Dry Pocket) | 17.7 |
| IrOx (Wet Pocket) | 11.3 |
| IrOx (PEG Pocket) | 11.8 |

*Reported values represent the average of values obtained in three dogs

*Reported values represent the average of values obtained in three dogs.

Tables 1 and 2, above, compare a platinum surface and an IrOx coated surface in terms of electrode interfacial impedance and polarization voltage as a function of shock number. An IrOx surface is somewhat less conductive and hence its overall impedance is greater than that of platinum and titanium at the beginning of administering shocks. However, as the cumulative number of shocks increases, the IrOx surface improves in impedance, perhaps as a result of better wetting by the Ringers lactate solution and its impedance is reduced somewhat. In comparison to platinum, the impedance of the IrOx is always greater. But compared to titanium where the oxide growth occurs as a result of greater number of shocks, the impedance of IrOx remains essentially stable. One important characteristic of a good electrode is electrical stability. In terms of polarization voltage, there are other factors that determine an electrode's performance besides impedance. In fact, the relatively large surface area of IrOx plays a major role in yielding a lower polarization voltage. The observation that the values of platinum and IrOx are nearly equivalent suggests that the high surface area of IrOx counteracts the relatively large impedance observed for IrOx, and therefore lowers its overall polarization voltage. The added benefit of IrOx over platinum becomes evident when its redox capabilities are taken into consideration.

Table 3 shows the results of an experiment performed in three canines, demonstrating embodiments of the invention. IrOx coated cans were employed as the counter electrode in assessing the defibrillation threshold of these canines. A pocket in a pectoral incision was made and the fluid around the walls of the pocket was wiped dry to simulate an essentially dry pocket. An IrOx coated can was placed in this pocket, sutured, and shocked against a transvenous IrOx coated lead electrode placed in the right ventricle, after fibrillation was induced in the animal. The lowest voltage obtained to defibrillate the dog was termed the defibrillation threshold. The pocket was subsequently, injected with saline solution and sutured. The defibrillation threshold was again measured. In the third case, the defibrillation threshold was measured when the pocket was dried again and this time a coating of low molecular weight polyethylene glycol, a lower molecular weight form of PEO, was applied to the surface of the can and in the pocket. The lowest defibrillation threshold was again measured.

Although data were obtained under acute experimental conditions, and a fibrotic capsule could not be formed within such a short time, it demonstrates the capabilities of the invention for actual human use. One can readily see that introducing a defibrillator unit exemplifying an embodiment of the present invention into a dry pocket, wetting the pocket (and hence, the pores of the oxide layers), and maintaining a good electrode to tissue interface significantly reduces the defibrillation threshold compared to prior art devices.

The use of PEG in a dry pocket is an important feature of the present invention. The polymer coated IrOx electrode conducts ions through the polymer and essentially replaces the saline solution as the carrier of the ionic species. The lower the molecular weight, the greater the conductivity and mobility of the ionic carrier. However, lower molecular weight polymers will tend to be unstable and could leach out or not provide very good interfaces. Higher molecular weight polymers are ideally suited for a good interface, but need to add plasticizer materials such as saline or other salts to maintain a high conductivity. In addition, the use of high molecular weight polymer allows indefinite retention of the salt solution and other desired materials, such as steroids, within the polymer matrix.

Referring to FIG. 5, surface 90 of conductive polyethylene oxide coat 70 is in continuous, direct contact with the adjacent body tissue 30, resulting in a very good interface 20. Conductive polymer coat 70 also completely fills and permeates the porous structure 112 resulting in the realization of the full beneficial potential of the IrOx layer 80.

Some of the advantages of using the new conductive polymer coated defibrillation electrode include: less tissue irritation than uncoated porous electrodes, and hence less fibrotic growth, thinner and more conductive fibrous layer, and stable chronic interface. The mixture of a steroid within the polymer matrix will significantly reduce the tissue irritation and will further help to maintain a good electrode/tissue interface. When it becomes necessary to remove one of the new implanted devices, the polymer coated unit should consistently be easier to remove since there will be less fibrotic growth on the polyethylene oxide surface overlying the IrOx. It is well known that a rough electrode surface can lead to scar tissue formation. Thus, in vivo use of the hot can electrode of the present invention, being coated with a polymeric interface, is expected to yield the benefit of a high surface area electrode and prevent scar tissue, in addition to the other advantages described above. The continuity of the interface is better than on an uncoated conventional porous surface, resulting in better distribution of current to the tissues to be stimulated.

The increased acceptability by the body of the new conductive PEG coated electrodes also provides anticoagulant effects and demonstrates reduced thrombogenicity, due in part to resistance of the coated electrode surface to protein adsorption and cell adhesion. The passage of current through an electrode placed against the heart, or other tissue, causes bruising and coagulation at the site. Further modifications of the new coatings by the inventor are expected to incorporate chemical or pharmaceutical agents that have thrombolytic, anti-thrombotic, anti-coagulant properties or that repel thrombotic factors, such as albumin, platelets, fibrinogen, and the like. These incorporated agents may be admixed in the polymeric matrix, or may be bonded to the polymer or to the surface of the polymer coated electrode.

EXAMPLE 3

Ionically Conductive Polymer Containing Inorganic Filler

According to another embodiment of the present invention, an ionically conductive polymeric material containing an inorganic filler is provided which is suitable for use on a defibrillator case having a porous outer surface, such as that described in Examples 1 and 2. The inorganic filler aids in enhancing the ionic transport of the ions through the polymeric material and in filling the pores of the can's surface to provide an electrically stable and oxidation resistant hot can electrode. Suitable inorganic fillers include materials such as high surface area alumina and high surface area silica. Preferably, the inorganic coating material is biocompatible, chemically and mechanically stable over several years and does not dissolve or leach out over time. The outer surface of the resulting can surface forms a smooth coating of the conductive material so that the interface with the tissue is complete, permitting the complete surface area of the electrode to be utilized and eliminating voids that would otherwise cause the DFT to increase with time and use.

Modifying the methods described in Examples 1 and 2, the filler is interdispersed into the polymeric solution at the time of mixing the polymer and salt solution. The coating material is then applied to the porous Pt or IrOx surface in a manner similar to that previously described.

EXAMPLE 4

Defibrillator with Ionically Conductive Polymer Coating

An improved implantable defibrillator in accordance with the present invention has a can that is coated with an insulating, non-conductive material such as parylene and has a window or opening in the insulative covering. The electrode portion of the hot can corresponds to the conducting surface exposed by the window, which serves to vectorize the current flow in a desired direction. U.S. Pat. No. 5,529,579, issued to Alt et al., describes a suitable basic defibrillator. According to the present invention, the can, or at least the portion exposed in the conductive window, is modified to include a coating of the conductive polymeric material of the present invention, as described in the examples above. The disclosure of U.S. Pat. No. 5,529,579 is incorporated herein by reference to the extent that it provides materials and methods not specifically set forth herein. The resulting hot can defibrillator provides, in addition to the features described in Examples 2 and 3, optimal current vectorization to the heart and low defibrillation threshold.

While certain embodiments of this invention have been shown and described in the foregoing examples, modifications thereof can be made by one skilled in the art without departing from the spirit or teaching of this invention. For instance, the concepts applied here to "hot cans" could easily be extended to other stimulation electrodes. The embodiments described herein are exemplary only and are not limiting. Many variations and modifications of the system and apparatus are possible and are within the scope of the invention. Accordingly, the scope of protection is not limited to the embodiments described herein, but is only limited by the claims that follow, the scope of which shall include all equivalents of the subject matter of the claims.

What is claimed is:

1. An implantable cardiac stimulus electrode comprising a coating of an ionically conductive polymeric composition comprising a polymer and an ionic medium wherein the polymer has a molecular weight from about 100,000 to about 10,000,000 daltons and wherein the ionic medium is adapted for reversible reduction-oxidation reactions and the composition has a conductive impedance value between 600 ohm to 22500 ohm measured at 100 Hz to 100 kHz.

2. The composition of claim 1, wherein the polymer is polyethylene oxide, polyethylene terpthalate, hydrogels, or polyacrylates.

3. The composition of claim 2, wherein the polymer is polyethylene oxide having a molecular weight of about 100,000–5,000,000 daltons.

4. The composition of claim 1, wherein the ionic medium is NaCl or another ionizable compound that does not alter a human recipient's body chemistry during the period of time that an electrode coated with said composition is implanted.

5. The composition of claim 1, further comprising at least one steroid, inorganic filler, antithrombotic agent, anticoagulant agent, anti-infection agent, or thrombolytic agent.

6. The composition of claim 1, wherein the ionically conductive polymeric composition comprises an electrically conductive ionic species.

7. The composition of claim 1, further comprising plasticizer salts.

8. The composition of claim 5, wherein the inorganic filler is alumina, silica, or a combination thereof.

* * * * *